United States Patent
Scheim et al.

(10) Patent No.: US 9,035,010 B2
(45) Date of Patent: May 19, 2015

(54) ORGANOSILICON COMPOUNDS AND THEIR USE FOR PRODUCING HYDROPHILIC SURFACES

(71) Applicant: Wacker Chemie AG, Munich (DE)

(72) Inventors: Uwe Scheim, Coswig (DE); Michael A. Brook, Ancaster (CA); Yang Chen, Ancaster (CA)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/376,764

(22) PCT Filed: Feb. 26, 2013

(86) PCT No.: PCT/EP2013/053786
§ 371 (c)(1),
(2) Date: Aug. 5, 2014

(87) PCT Pub. No.: WO2013/127771
PCT Pub. Date: Sep. 6, 2013

(65) Prior Publication Data
US 2014/0371416 A1 Dec. 18, 2014

(30) Foreign Application Priority Data
Mar. 1, 2012 (DE) .......... 10 2012 203 267

(51) Int. Cl.
| | |
|---|---|
| C09D 183/08 | (2006.01) |
| C08G 77/26 | (2006.01) |
| C08J 3/24 | (2006.01) |
| C07F 7/08 | (2006.01) |
| C07F 7/18 | (2006.01) |
| C08J 7/12 | (2006.01) |

(52) U.S. Cl.
CPC ............ *C09D 183/08* (2013.01); *C07F 7/1836* (2013.01); *C08J 7/12* (2013.01); *C08J 2383/02* (2013.01); *C07F 7/0818* (2013.01); *C08G 77/26* (2013.01); *C08J 3/24* (2013.01); *C08J 2383/08* (2013.01)

(58) Field of Classification Search
None
See application file for complete search history.

(56) References Cited

FOREIGN PATENT DOCUMENTS

WO 2011022827 A1 3/2011

OTHER PUBLICATIONS

Terence D. Blake, Dynamic Contact Angles and Wetting Kinetics, Wettability edited by John C. Berg, 1993, pp. 252-309, Surfactant Science Series vol. 49, Marcel Dekker, Inc.
Jing Li et al., Synthesis of Polyethylene Glycol (PEG) Derivatives and PEGylated-Peptide Biopolymer Conjugates, Biomacromolecules, 2003, pp. 1055-1067, vol. 4, American Chemical Society.

*Primary Examiner* — Robert S Loewe
(74) *Attorney, Agent, or Firm* — Brooks Kushman P.C

(57) ABSTRACT

Compounds of the formula (I)

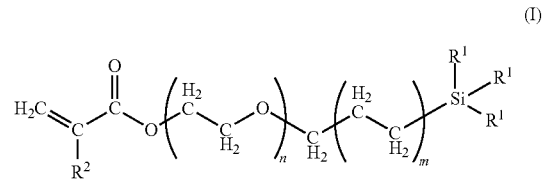

where $R^1$ each individually is identical or different and is a hydrocarbon radical, $R^2$ each individually is hydrogen or a methyl radical, n is an integer from 6 to 11, and m is 0 or 1, with the proviso that the sum of the number of carbon atoms in the three radicals $R^1$ in the compound of the formula (I) is 6 to 24, can be admixed with curable polymer compositions to form products with hydrophilic surfaces, or can be applied to surfaces to render them hydrophilic.

16 Claims, No Drawings

ORGANOSILICON COMPOUNDS AND THEIR USE FOR PRODUCING HYDROPHILIC SURFACES

CROSS-REFERENCE TO RELATED APPLICATIONS

This application is the U.S. National Phase of PCT Appln. No. PCT/EP2013/053786 filed Feb. 26, 2013, which claims priority to German application DE 10 2012 203 267.3 filed Mar. 1, 2012, the disclosures of which are incorporated in their entirety by reference herein.

BACKGROUND OF THE INVENTION

1. Field of the Invention

The invention relates to organosilicon compounds, to processes for producing them, to their use for producing hydrophilic surfaces, and to silicone elastomers with hydrophilic surfaces. In particular, the invention relates to compounds which, when added to curable mixtures, provide, after curing, a hydrophilic surface, or which can be applied after curing to the surface of the silicone elastomers, in which case they are anchored to the surface and thereby give the silicone elastomers a hydrophilic surface.

2. Description of the Related Art

Polydimethylsiloxane elastomers are, depending on the formulation, soft, very flexible materials with a series of advantageous properties such as extraordinary thermal and electric stability, high optical transparency, good gas permeability and high elasticity, even at very low temperatures. The high hydrophobicity of these elastomers is also often advantageous for applications where water repellency is desired. However, the low surface energy which polydimethylsiloxane surfaces exhibit can also be disadvantageous, particularly if biological units absorb at the surface. For example, the hydrophobicity, i.e. poor wettability of the surface of polydimethylsiloxanes is responsible for the surfaces becoming susceptible to so-called "fouling" by proteins or lipids. Organisms are able, with surprising stubbornness, to adhere to silicone surfaces and then to multiply.

By contrast, biological molecules and organisms exhibit a considerably less efficient adherence to certain types of hydrophilic surfaces. For example, poly(ethylene glycol) (PEG)-modified surfaces are known for repelling proteins and reducing cell adhesion. Other strategies such as the anchoring of polysaccharides, proteins and surface-active molecules likewise reduce the tendency of polymer surfaces towards fouling.

Primarily two strategies have been pursued in order to enhance the hydrophilicity of silicone surfaces. The first involves oxygen plasma treatment, UV irradiation and corona discharge, with superficial OH groups being produced in all methods. One disadvantage of this procedure is that the surface can become damaged as a result, as well as expenditure on apparatus which is required to implement this treatment. Alternatively, hydrophilic materials can be absorbed on the surface, bound to the surface (e.g. poly(ethylene glycol)) or be incorporated into the material by copolymerization. All these strategies have disadvantages. Silicone polymers have high mobility and exhibit surface reversion, during which the hydrophilic materials again end up underneath the mobile silicone polymers since the latter migrate with the interface to the air. Although silicone elastomer surfaces can be made hydrophilic such that even contact angles of 0° are achieved, the hydrophobicity of the surfaces is generally regenerated within a short time.

In order to overcome this problem, it was proposed in WO-A 11022827 to bond allyl-modified polyethylene glycols of the structure

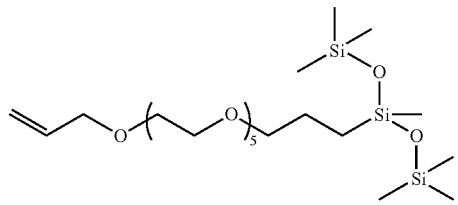

onto silicone surfaces by addition onto superficial Si—H groups by means of hydrosilylation. At a comparatively high concentration of these groups on the surface, contact angles of less than 10° could thus be achieved. However, these compounds are subject to a hydrolytic cleavage of the trisiloxane group, whereupon the hydrophilicity of the surface is as a result significantly reduced again over the course of time. Moreover, these compounds are only suitable for modifying Si—H-containing surfaces.

SUMMARY OF THE INVENTION

It has now been surprisingly discovered that compounds bearing an oligo(ethylene glycol) chain which carry an acrylic acid function at one end and a triorganosilyl group at the other end are able, in an exceptional manner, to generate permanent hydrophilicity, particularly on silicone surfaces.

DETAILED DESCRIPTION OF THE PREFERRED EMBODIMENTS

The invention thus provides compounds of the formula

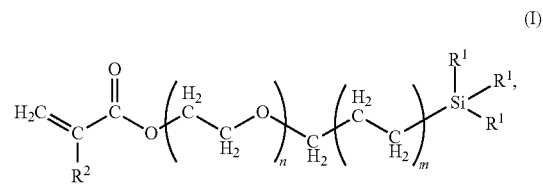

where
$R^1$ can be identical or different and is a hydrocarbon radical,
$R^2$ is hydrogen or a methyl radical,
n is an integer from 6 to 11 and
m is 0 or 1,
with the proviso that the sum of the number of carbon atoms in the three radicals $R^2$ in the compound of the formula (I) is 6 to 24.

Examples of radicals $R^2$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical, isooctyl radicals and the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and the 2-propenyl radical; aryl radicals, such as the phenyl, naphthyl, anthryl and phenanthryl radicals; alkaryl radicals such as the o-, m-, p-tolyl radicals, xylyl radicals, and ethylphenyl radicals; and aralkyl radicals such as the benzyl radical and the α- and the β-phenylethyl radicals.

Preferably, radical $R^1$ are alkyl radicals having 1 to 12 carbon atoms, more preferably ethyl, n-propyl, n-butyl, n-pentyl or n-hexyl radicals, and in particular the n-hexyl radical.

Preferably, each of the radicals $R^1$ in formula (I) are the same.

Preferably, n is 6, 7, 8 or 9.

Examples of compounds according to the invention of the formula (I) are

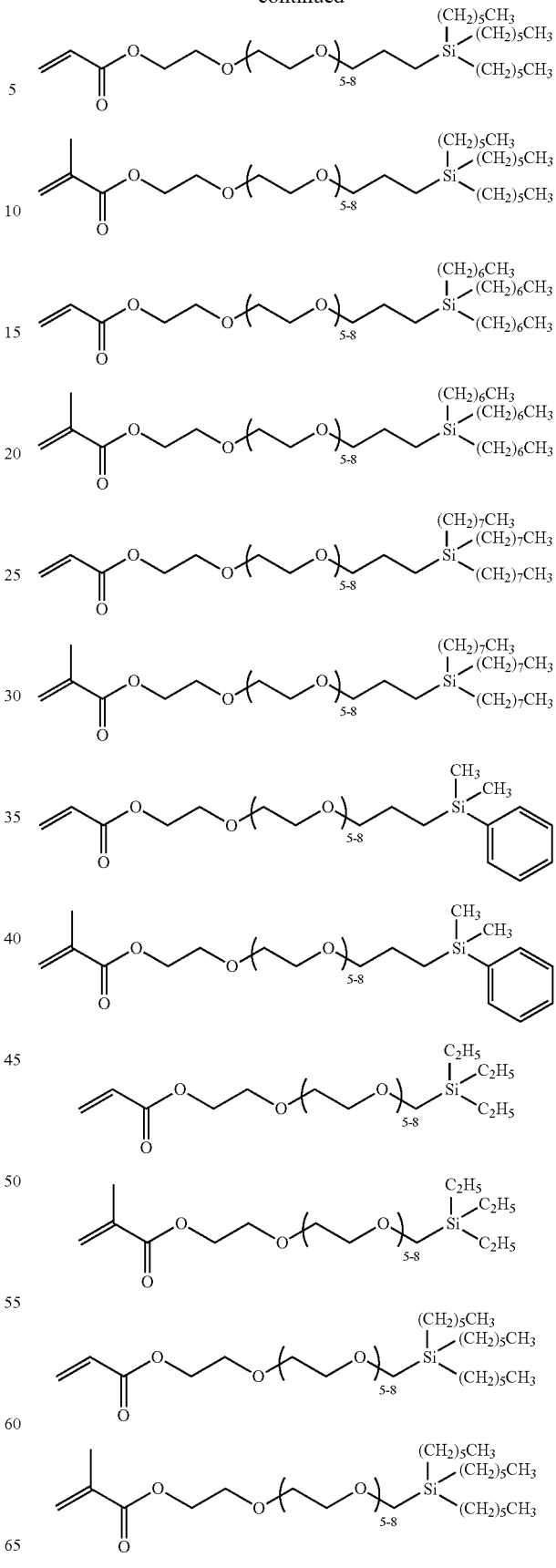

Preferably, the compounds according to the invention are

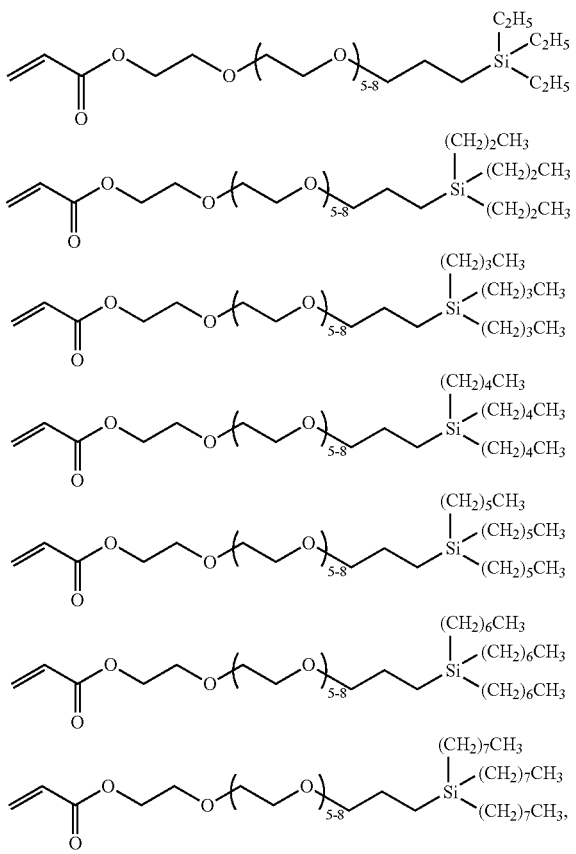

more preferably

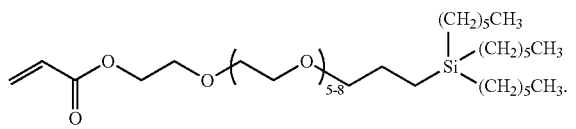

At room temperature and 1013 hPa, the compounds according to the invention are preferably water-clear to slightly cloudy, colorless to yellowish liquids.

The compounds according to the invention of the formula (I) can be produced by methods customary in chemistry. For example, firstly the silyl-substituted polyether can be produced by addition of trialkylsilanes onto standard commercial polyethylene glycols allyl-terminated at one end, catalyzed with tris(triphenylphosphine)rhodium (I) chloride. The polyethylene glycol terminated at one end by 3-trialkylsilylpropyl groups produced in this way is then reacted with acryloyl chloride or methacryloyl chloride in the presence of an HCl acceptor in a solvent, such as e.g. triethylamine in diethyl ether.

The invention further provides a process (process 1) for producing the compounds of the formula (I), preferably where m=1, by addition of triorganylsilanes onto polyethylene glycols which carry an OH group on one end and have radicals with aliphatic carbon-carbon multiple bonds on the other end, in the presence of catalyst promoting the addition of Si-bonded hydrogen onto aliphatic multiple bond, and subsequent reaction with acryloyl chloride or methacryloyl chloride.

The organyl groups of the silanes used in process 1 according to the invention are SiC-bonded hydrocarbons, preferably the radicals specified for radical $R^1$.

The process 1 according to the invention can be carried out under the same conditions as the hydrosilylation processes known hitherto.

The process 1 according to the invention is preferably carried out at temperatures between 20 and 100° C. at the pressure of the ambient atmosphere, i.e. as a rule about 1013 hPa. Preferably, the hydrosilylation, preferably the reaction of α-allyl-ω-hydroxypoly(ethylene glycol) with trialkylsilane, is carried out without the addition of a solvent.

The catalyst used in the process 1 according to the invention is preferably tris(triphenylphosphine)rhodium (I) chloride.

After hydrosilylation has taken place, the reaction mixture can be worked up by processes known hitherto. Preferably, in this respect, the reaction product is taken up in a water-miscible solvent, preferably THF, and admixed with water and a small amount of an acid, in order for example to eliminate Si—O—C bonds formed which can form as a result of the reaction of the OH group of the polyether with Si-bonded hydrogen. When the reaction is complete, which lasts about 12 hours at room temperature, the acid is preferably neutralized, preferably using MgO. Finally, the solvent, preferably THF and water, is preferably removed and the residue is taken up with acetonitrile. The siloxanes formed as by-product can be removed by extracting the acetonitrile solution of the product with n-hexane. Further purification of the product can take place by means of treatment with silica gel.

Preferably, for the reaction of the resulting silyl-group-terminated polyethylene glycol, in particular of the polyethylene glycol terminated with 3-trialkylsilylpropyl groups, with acryloyl chloride or methacryloyl chloride, a solvent and an HCl acceptor are used where the HCl acceptor is preferably a tertiary amine and the solvent is preferably diethyl ether. The amine hydrochloride that is formed in the process can then be separated off by filtration.

In a further possible process (process 2) for producing the compounds according to the invention of the formula (I) where m=0, firstly a hydroxymethyltriorganylsilane is reacted with ethylene oxide in the presence of catalysts known per se (bases, zinc hexacyanocobaltate). The polyethylene glycols closed at one end with a triorganylsilylmethyl group obtained in this way are then reacted with acryloyl chloride or methacryloyl chloride in the presence of e.g. triethylamine in diethyl ether as solvent to give the target compounds of the formula (I).

The invention further provides a process (process 2) for producing the compounds according to the invention of the formula (I) where m=0, characterized in that firstly a hydroxymethyltriorganylsilane is reacted with ethylene oxide and the resulting polyethylene glycol terminated at one end with a triorganylsilylmethyl group is then reacted with acryloyl chloride or methacryloyl chloride.

Preferably, in process 2 according to the invention, the reaction of hydroxymethyltriorganylsilane with ethylene oxide is carried out in the presence of catalysts, such as e.g. bases, zinc hexacyanocobaltate.

Preferably, in process 2 according to the invention, the reaction of the polyethylene glycol terminated at one end with a triorganylsilylmethyl group with acryloyl chloride or methacryloyl chloride is carried out in the presence of solvents.

The components used in the processes according to the invention can in each case be one type of such as component as well as a mixture of at least two types of a particular component.

The components used in the processes according to the invention are standard commercial products and/or can be produced by processes customary in chemistry.

The compounds of the formula (I) according to the invention or produced according to the invention can now be used for any desired purposes, such as e.g. for the surface modification of substrates and articles.

The compounds of the formula (I) according to the invention are preferably reacted with amino-functional alkoxysil (oxan)yl components.

The invention further provides reaction products (U) obtainable by reacting compounds of the formula (I) with organosilicon compounds (B) comprising at least one unit of the formula $$D_c Si(OR)_b R^3_a O_{(4-a-b-c)/2} \quad (II),$$

in which
  $R^3$ can be identical or different and is a monovalent, optionally substituted, SiC-bonded organic radical free from basic nitrogen,
  R can be identical or different and is hydrogen or an optionally substituted hydrocarbon radical,
  D can be identical or different and is a monovalent, SiC-bonded radical comprising at least one group $—NHR^4$ where $R^4$ is hydrogen or an optionally substituted hydrocarbon radical,
  a is 0, 1, 2 or 3, preferably 1,
  b is 0, 1, 2 or 3, preferably 1, 2 or 3, more preferably 2 or 3, and
  c is 0, 1, 2, 3 or 4, preferably 1,
with the proviso that the sum of a+b+c is less than or equal to 4 and organosilicon compound (B) comprises at least one radical of the formula (II) with at least one radical D.

The invention further provides a process for producing the reaction products (U) by reacting compounds of the formula (I) with organosilicon compounds (B) comprising at least one unit of the formula (II).

The organosilicon compounds used according to the invention (B) may either be silanes (B1), i.e. compounds of the formula (II) where a+b+c=4, as well as siloxanes (B2), i.e. structures containing at least one unit of the formula (II) where a+b+c≤3.

Examples of radical $R^3$ are the examples given for $R^1$.

Radicals $R^3$ are preferably hydrocarbon radicals having 1 to 18 carbon atoms, more preferably hydrocarbon radicals having 1 to 5 carbon atoms, and in particular the methyl radical.

Examples of optionally substituted hydrocarbon radicals R are the examples given for radical $R^1$, as well as radicals $CH_3OCH_2CH_2—$, $CH_3CH_2OCH_2CH_2—$, $CH_3OCH_2CH_2OCH_2CH_2—$ and $CH_3CH_2OCH_2CH_2OCH_2CH_2—$.

The radicals R are preferably hydrogen or hydrocarbon radicals having 1 to 18 carbon atoms, which can be interrupted by one or more oxygen atoms, more preferably hydrogen or hydrocarbon radicals having 1 to 10 carbon atoms, in particular the methyl and the ethyl radical.

Examples of optionally substituted hydrocarbon radicals $R^4$ are the examples given for radical $R^1$ which can be substituted with $NH_2$ groups or can be interrupted by NH groups.

The radicals $R^4$ are preferably hydrogen or hydrocarbon radicals having 1 to 18 carbon atoms which can be substituted with $NH_2$ groups or interrupted by NH groups. Radical $R^4$ is most preferably hydrogen, n-butyl, 2-aminoethyl, N-(2-aminoethyl)-2-aminoethyl, or cyclohexyl.

Examples of radicals D are radicals of the formulae $H_2N(CH_2)_3—$, $H_2N(CH_2)_2NH(CH_2)_3—$, $H_2N(CH_2)_2NH(CH_2)_2$ $NH(CH_2)_3—$, $H_3CNH(CH_2)_3—$, $C_2H_5NH(CH_2)_3—$, $C_3H_7NH(CH_2)_3—$, $C_4H_9NH(CH_2)_3—$, $C_5H_{11}NH(CH_2)_3—$, $C_6H_{13}NH(CH_2)_3—$, $C_7H_{15}NH(CH_2)_3—$, $H_2N(CH_2)_4—$, $H_2N—CH_2—CH(CH_3)—CH_2—$, $H_2N(CH_2)_5—$, cyclo-$C_5H_9NH(CH_2)_3—$, cyclo-$C_6H_{11}NH(CH_2)_3—$, phenyl-NH$(CH_2)_3—$, $H_2N(CH_2)—$, $H_2N(CH_2)_2NH(CH_2)—$, $H_2N(CH_2)_2NH(CH_2)_2NH(CH_2)—$, $H_3CNH(CH_2)—$, $C_2H_5NH(CH_2)—$, $C_3N_7NH(CH_2)—$, $C_4H_9NH(CH_2)—$, $C_5H_{11}NH(CH_2)—$, $C_6H_{13}NH(CH_2)—$, $C_7H_{15}NH(CH_2)—$, cyclo-$C_5H_9NH(CH_2)—$, cyclo-$C_6H_{11}NH(CH_2)—$, phenyl-NH$(CH_2)—$, $(CH_3O)_3Si(CH_2)_3NH(CH_2)_3—$, $(C_2H_5O)_3Si(CH_2)_3NH(CH_2)_3—$, $(CH_3O)_2(CH_3)Si(CH_2)_3NH(CH_2)_3—$ and $(C_2H_5O)_2(CH_3)Si(CH_2)_3NH(CH_2)_3—$.

Radicals D preferably SiC-bonded hydrocarbon radicals with at least one group $—NHR^4$, particularly preferably the $H_2N(CH_2)_3—$, $H_2N(CH_2)_2NH(CH_2)_3—$, cyclo-$C_6H_{11}NH(CH_2)_3—$, n-$C_4H_9NH(CH_2)—$ and cyclo-$C_6H_{11}NH(CH_2)—$ radical.

Examples of the silanes optionally used according to the invention (B1) are $H_2N(CH_2)_3—Si(OCH_3)_3$, $H_2N(CH_2)_3—Si(OC_2H_5)_3$, $H_2N(CH_2)_3—Si(OCH_3)_2CH_3$, $H_2N(CH_2)_3—Si(OC_2H_5)_2CH_3$, $H_2N(CH_2)_2NH(CH_2)_3—Si(OCH_3)_3$, $H_2N(CH_2)_2NH(CH_2)_3—Si(OC_2H_5)_3$, $H_2N(CH_2)_2NH(CH_2)_3—Si(OC_2H_5)_2CH_3$ n-$C_4H_9NH(CH_2)—Si(OCH_3)_3$, n-$C_4H_9NH(CH_2)—Si(OC_2H_5)_2CH_3$ n-$C_4H_9NH(CH_2)—Si(OCH_3)_2CH_3$, n-$C_4H_9NH(CH_2)—Si(OC_2H_5)_3$, n-$C_4H_9NH(CH_2)—Si(OCH_3)_3$, n-$C_4H_9NH(CH_2)—Si(OC_2H_5)_2CH_3$n-$C_4H_9NH(CH_2)—Si(OCH_3)_2CH_3$, cyclo-$C_6H_{11}NH(CH_2)—Si(OC_2H_5)_3$, cyclo-$C_6H_{11}NH(CH_2)—Si(OCH_3)_3$, cyclo-$C_6H_{11}NH(CH_2)—Si(OC_2H_5)_2CH_3$ cyclo-$C_6H_{11}NH(CH_2)—Si(OCH_3)_2CH_3$, cyclo-$C_6H_{11}NH(CH_2)—Si(OC_2H_5)_3$, cyclo-$C_6H_{11}NH(CH_2)—Si(OCH_3)_3$, cyclo-$C_6H_{11}NH(CH_2)—Si(OC_2H_5)_2CH_3$ cyclo-$C_6H_{11}NH(CH_2)—Si(OCH_3)_2CH_3$ and cyclo-$C_6H_{11}NH(CH_2)—Si(OC_2H_5)_3$.

The siloxanes (B2) may be pure siloxanes, i.e. compounds consisting of units of the formula (II) or else a siloxane matrix, i.e. a material with at least one chemically bonded unit of the formula (II).

Examples of component (B2) are polydimethylsiloxanes in which at least one methyl group is replaced by a radical D. Further examples are methylsilicone resins in which at least one methyl group is replaced by a radical D, as well as elastomeric polydimethylsiloxane networks in which at least one methyl group is replaced by a radical D.

The reaction according to the invention (Michael addition) takes place at temperatures of preferably 15 to 100° C., particularly preferably at room temperature, and preferably at the pressure of the ambient atmosphere, i.e. at approximately 800 to 1100 hPa.

In the reaction according to the invention, compounds of the formula (I) and NH or $NH_2$ groups present in the organosilicon compounds (B) are preferably used in a molar ratio of 1:1 to 2:1, particularly preferably 1:1.

If for example component (B) comprises $NH_2$ groups, there is the possibility of the reaction with compounds of the formula (I) in the molar ratio of 1:1 or 1:2, in the case of NH groups naturally only 1:1.

The components used in the process according to the invention can in each case be one type of such a component as well as a mixture of at least two types of a particular component.

The components (B) used in the process according to the invention are standard commercial products and/or can be produced by processes customary in chemistry.

Examples of reaction products according to the invention are

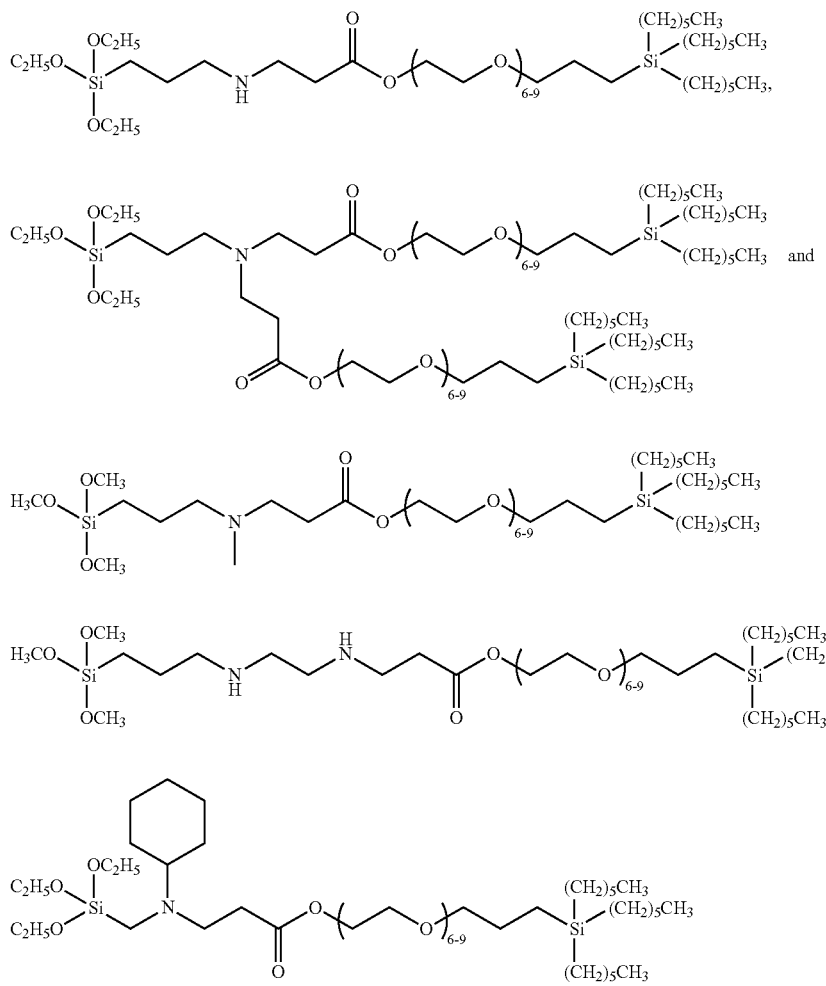

and surfaces which have at least one covalently bonded radical, which is produced by the reaction of the amino group in radical D of the formula (II) with compounds of the formula (I), such as for example

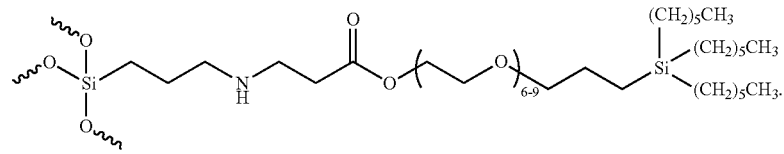

The reaction products (U) according to the invention can be used and/or produced everywhere where hydrophilicity is to be generated, such as for example in crosslinkable compositions and for modifying surfaces.

Thus, it is possible to directly add the reaction products according to the invention (U) to still not cured silicone elastomer mixtures. Furthermore, it is possible to produce the reaction products (U) in the still not cured silicone elastomer mixtures by adding the compounds of the formula (I) according to the invention and the corresponding aminosilanes (B1) in the desired molar ratio to the mixtures. The order of addition of the individual components here is unimportant. The hydrophilic surface is formed here in each case after curing the crosslinkable compositions.

The invention further provides crosslinkable compositions comprising reaction product (U) according to the invention or compound of the formula (I) together with component (B).

The compositions according to the invention can be any desired compositions that can be crosslinked by condensation to give elastomers and are based on organosilicon compounds, for example, single-component or two-component vulcanizable organopolysiloxane compositions. The crosslinkable compositions here can be free from fillers, but can also comprise active or inactive fillers.

The type and amount of the components usually used in such compositions are already known. Preferably, the crosslinkable compositions according to the invention are those which optionally, besides reaction product (U) or compound of the formula (I) together with component (B), organopolysiloxanes with at least two condensable radicals, comprise crosslinkers with at least three hydrolysable radicals, optionally condensation catalyst, optionally fillers and optionally additives.

The compositions according to the invention are preferably single-component compositions that are storable under exclusion of water and crosslinkable at room temperature upon ingress of water (RTV-1). The compositions according to the invention can, however, also be two-component compositions crosslinkable by condensation reaction.

The crosslinking of the compositions according to the invention can be carried out under the conditions known for this purpose. Thus e.g. in the case of the particularly preferred RTV-1 compositions, the customary water content of the air suffices, with the crosslinking preferably being carried out at room temperature and the pressure of the ambient atmosphere, i.e. about 900 to 1100 hPa.

The present invention further provides moldings produced by crosslinking the compositions according to the invention.

In a further embodiment, the compounds according to the invention of the formula (I), following curing of aminosilane-containing silicone elastomer mixtures, are subsequently applied to the silicone elastomer surfaces (B2) and left to react. In a further embodiment, the reaction products according to the invention (U) and/or a mixture of compound of the formula (I) and component (B1) are applied to the surface of cured silicone elastomer surfaces, in which case the silicone elastomers can contain further aminosilanes, but can also be free from aminosilanes. In a further embodiment, aminosilanes (B1) can firstly be applied to cured amine-free silicone elastomer surfaces, thus producing component (B2). Then, the compounds according to the invention of the formula (I) are applied and left to react.

The invention further provides a process for modifying surfaces of substrates by applying the reaction products according to the invention (U) and/or a mixture of compound of the formula (I) and component (B) to the surface of the substrate and leaving them to react.

The substrates used according to the invention are preferably cured silicone elastomers, glass surfaces, surfaces of silicatic building materials, such as concrete, stoneware and porcelain, or metals, such as steel and aluminum, as well as plastics, such as PVC, PMMA and polycarbonate.

In all cases where the reaction products (U) or compounds of the formula (I) and component (B1) are applied to substrate surfaces, the use of an organic solvent, such as e.g. mixtures of aliphatic hydrocarbons, obtainable for example under the trade name "Shellsol D60", or ethers, such as e.g. tetrahydrofuran, is preferred. A further preferred variant is the use of the reaction products (U) or of the mixtures of compounds of the formula (I) with component (B1) in aqueous solution or as emulsion. The application of the particular substance can take place by known methods, such as, for example, by brushing, wiping, spraying, application using a roller or immersion.

After treatment of the surfaces has taken place, these can be freed from the optionally used solvents in a manner known per se, such as for example by so-called natural drying, i.e. evaporation at room temperature and pressure of the ambient atmosphere.

The surfaces modified according to the invention are permanently hydrophilic, which can be seen easily from the contact angle, which is reduced by up to values of 20° depending on the amount and type of compounds applied.

Determination of the contact angle is already known. In this method, the contact angle $\theta$ of a fluid phase (2) on a fixed phase (3) with a second fluid phase (1) as surrounding phase is measured. In this regard, reference may be made e.g. to "Wettability" edited by John C. Berg, Surfactant Series Volume 49; Marcell Dekker Inc. 1993 ISBN 0-8247-9046-4, Chapter 5, T. D. Blake: "Dynamic Contact Angle and Wetting Kinetics", in particular on p. 252, $1^{st}$ paragraph and FIG. 1b.

Moreover, the invention relates to further processes for hydrophilizing surfaces of objects by applying compounds of the formula (I), with the proviso that groups which can react with the acrylic acid function must be present on the surface of these objects.

The compounds according to the invention of the formula (I) have the advantage that they are easy to produce and have a very strong hydrophilizing effect even in a small amount, even if the compounds are added to crosslinkable compositions. Moreover, the effect is also retained over a prolonged period, i.e. it is not reduced by virtue of the fact that the hydrophilizing layer becomes hydrophobic again as a result of migrating siloxanes.

The reaction products according to the invention (U) have the advantage that they impart a permanent hydrophilicity to siloxane elastomer surfaces even in small amounts.

In the examples described below, all viscosity data refers to a temperature of 25° C. Unless stated otherwise, the examples below are carried out at a pressure of the ambient temperature, i.e. approximately at 1000 hPa, and at room temperature, i.e. at about 23° C., or at a temperature which is established upon combining the reactants at room temperature without additional heating or cooling, as well as at a relative atmospheric humidity of about 50%. Furthermore, unless stated otherwise, all data relating to parts and percentages is based on the weight.

In the examples below, the contact angles were carried out on a Ramé Hart NRL CA Goniometer. The water used had a conductivity of 18 MΩ19 cm. Drops with a volume of 20 µl were used.

The Shore A hardness is determined in accordance with DIN (German Industry Standard) 53505 (edition from August 2000).

Samples of the examples below were stored at 23° C. and 50% relative atmospheric humidity, unless stated otherwise.

Example 1

α-Acryloyl-ω-triethylsilylpropylpoly(ethylene glycol) [APC2]

Dry air was passed at room temperature through a mixture of 9.38 g (24 mmol) of α-allyl-ω-hydroxypoly(ethylene glycol) with a molecular weight of about 390 g/mol, 2.98 g (25 mmol) of triethylsilane and 0.0448 g of Wilkinson catalyst (tris(triphenylphosphine)rhodium(I) chloride) for 1 hour. The mixture was then further stirred at room temperature for a period of 12 hours. Then, a solution consisting of 1.0 g of acetic acid, 1 ml of dist. water and 50 ml of THF was added and the mixture was stirred for a further 5 hours at room temperature. Finally, 5 g of MgO were added, then the solid was filtered off and the THF was drawn off in vacuo at 10 mbar. The residue was dissolved in acetonitrile. This solution was extracted with hexane (3 times 10 ml). The hexane phase was discarded. The acetonitrile was then distilled off under reduced pressure. The residue was further purified by passing it through a short column filled with silica gel, using a mixture of methylene chloride/hexane (1:1) as eluent. After evaporating off the solvent, 9.1 g (74%) of pure α-hydroxy-ω-triethylsilylpropylpolyethylene glycol were obtained.

8.0 g (15.9 mmol) of the thus obtained α-hydroxy-ω-triethylsilylpropylpolyethylene glycol and 16.2 g (159 mmol) of triethylamine were dissolved in 200 ml of diethyl ether. Over the course of 30 min, 1.6 ml (17.5 mmol) of acryloyl chloride were added dropwise to this solution with stirring at 0° C. When addition was complete, the cooling was removed and the mixture was further stirred for a period of 12 hours at room temperature. The mixture was then separated off from the precipitated solid and the ethereal solution was freed from the solvent under reduced pressure. The residue was in turn purified over a silica gel column using methylene chloride/hexane as eluent. 7.63 g (81%) of the desired target product α-acryloyl-ω-triethylsilylpropylpoly(ethylene glycol) were thus obtained. The total yield of both steps was 60%.

Example 2

α-Acryloyl-ω-tri-n-hexylsilylpropylpoly(ethylene glycol) [APC6]

The experiment as per Example 1 was repeated using firstly 9.98 g (28.5 mmol) of α-allyl-ω-hydroxypoly(ethylene glycol) with a molecular weight of about 390 g/mol and 9.12 g (31.4 mmol) of tri-n-hexylsilane. 9.8 g (53.5%) of pure α-hydroxy-ω-tri-n-hexylsilylpropylpolyethylene glycol were obtained, of which 8.0 g (11.9 mmol) were reacted as per the procedure described in Example 1 with acryloyl chloride to give 6.9 g (78%) of target product α-acryloyl-ω-tri-n-hexylsilylpropylpoly(ethylene glycol). The total yield of both steps was 41.7%.

Example 3

α-Acryloyl-ω-tri-n-octylsilylpropylpoly(ethylene glycol) [APC8]

The procedure described in Example 1 was repeated using 3.53 g (9.1 mmol) of α-allyl-ω-hydroxypoly(ethylene glycol) with a molecular weight of about 390 g/mol and 3.69 g (10.0 mmol) of tri-n-octylsilane. 2.69 g (39%) of pure α-hydroxy-ω-tri-n-octylsilylpropylpolyethylene glycol were obtained, of which 2.0 g (2.64 mmol) were reacted as per the procedure described in Example 1 with acryloyl chloride to give 1.65 g (75%) of target product α-acryloyl-ω-tri-n-octylsilylpropylpoly(ethylene glycol). The total yield of both steps was 29.2%.

Examples 4-6

1.0 g of an α,ω-dihydroxypolydimethylsiloxane with a viscosity of 2000 mPas were mixed, at 25° C., with 0.024 g of aminopropyltriethoxysilane and the amounts, given in Table 1, of the acryloxy-functional polyethylene glycols produced as per Examples 1 to 3. The amounts were calculated such that 2 mol of the acryloxy-functional compounds were present per mole of aminopropyltriethoxysilane. 0.0035 g of dibutyltin dilaurate were then added and the mass was intensively mixed for 1 min and poured into a small Petri dish so that for example a layer thickness of 1 mm was obtained. After 24 hours, all of the mixtures were cured to a silicone elastomer with a Shore A hardness of 10. The contact angles of a water drop (20 μl) were then measured as a function of the time. The results are summarized in Table 1.

Comparative Example C1

1.0 g of an α,ω-dihydroxypolydimethylsiloxane with a viscosity of 2000 mPas were mixed, at 25° C., with 0.024 g of aminopropyltriethoxysilane and 0.09 g of a methoxypoly (ethylene glycol)monoacrylate (CAS No. 32171-39-4, molecular weight $M_n$ about 480 g/mol, obtainable under the number 454990 from Sigma-Aldrich, referred to in Table 1 as "APM"). 0.0035 g of dibutyltin dilaurate were then added and the mass was intensively mixed for 1 min and poured into a small Petri dish such that for example a layer thickness of 1 mm was obtained. After 24 hours, the mixtures were cured to a silicone elastomer with a Shore A hardness of 10. The contact angles of a water drop (20 μl) were then measured as a function of time. The results are summarized in Table 1.

TABLE 1

| Example | Compound | Amount [g] | Contact angle in °, measured after | | | | | | | | | |
|---|---|---|---|---|---|---|---|---|---|---|---|---|
| | | | 1 min | 2 min | 3 min | 4 min | 5 min | 6 min | 7 min | 8 min | 9 min | 10 min |
| 4 | APC2 | 0.12 | 43 | 35 | 29 | 25 | 22 | 19 | 18 | 16 | 13 | 11 |
| 5 | APC6 | 0.16 | 36 | 29 | 28 | 25 | 23 | 21 | 19 | 17 | 15 | 12 |
| 6 | APC8 | 0.18 | 38 | 33 | 31 | 31 | 30 | 30 | 30 | 30 | 29 | 29 |
| C1 | APM | 0.09 | 77 | 76 | 73 | 70 | 67 | 67 | 66 | 65 | 63 | 63 |

Examples 7-9

1.0 g of an α,ω-methyldimethoxysilyl-terminated polydimethylsiloxane with a viscosity of 80,000 mPas was mixed, at 25° C., with 0.024 g of aminopropyltriethoxysilane and the amounts, given in Table 2, of the acryloxy-functional polyethylene glycols produced as per Examples 1 to 3. The amounts were calculated such that 2 mol of the acryloxy-functional compounds were present per mole of aminopropyltriethoxysilane. 0.003 g of a tin catalyst (produced by reacting 4 parts by weight of tetraethoxysilane with 2.2 parts by weight of dibutyltin diacetate, where the ethyl acetate formed was distilled off) was then added and the mass was intensively mixed for 1 min and poured into a small Petri dish such that for example a layer thickness of 1 mm was obtained.

The material cured under the action of atmospheric humidity. After 24 hours, all of the mixtures had cured to a silicone elastomer. The contact angles of a water drop (20 μl) were then measured as a function of the time. The results are summarized in Table 2.

TABLE 2

| | | | Contact angle in °, measured after | | | | | | | | |
|---|---|---|---|---|---|---|---|---|---|---|---|
| Example | Compound | Amount [g] | 1 min | 2 min | 3 min | 4 min | 5 min | 6 min | 7 min | 8 min | 9 min | 10 min |
| 7 | APC2 | 0.12 | 58 | 49 | 48 | 46 | 42 | 40 | 38 | 36 | 34 | 31 |
| 8 | APC6 | 0.16 | 31 | 28 | 24 | 22 | 21 | | | 19 | 18 | 18 |
| 9 | APC8 | 0.18 | | | 45 | 43 | 40 | 38 | 37 | 35 | 34 | 34 |

Examples 10-12

1.0 g of an α,ω-methyldimethoxysilyl-terminated polydimethylsiloxane with a viscosity of 80,000 mPas was mixed, at 25° C., with the amounts, given in Table 3, of N-methyl-3-aminopropyltrimethoxysilane and the amounts, given in Table 3, of the α-acryloyl-ω-triethylsilylpropylpoly(ethylene glycol) [APC2] produced as per Example 1. The amounts were calculated such that 1 mole of the acryloxy-functional compounds was present per mole of N-methyl-3-aminopropyltrimethoxysilane. Then, 0.003 g of a tin catalyst (produced by reacting 4 parts by weight of tetraethoxysilane with 2.2 parts by weight of dibutyltin diacetate, with the ethylacetate formed being distilled off) was added and the mass was intensively mixed for 1 min and poured into a small Petri dish such that for example a layer thickness of 1 mm was obtained. The material cures under the action of atmospheric humidity. After 24 hours, all of the mixtures had cured to a silicone elastomer. The contact angles of a water drop (20 μl) were then measured after 10 min. The results are summarized in Table 3.

TABLE 3

| Example | Compound | Amount [mg] | Amount of N-methyl-3-aminopropyl-trimethoxysilane | Contact angle measured after 10 min |
|---|---|---|---|---|
| 10 | APC2 | 61 | 21 mg | 39° |
| 11 | APC2 | 30 | 11 mg | 48° |
| 12 | APC2 | 15 | 5 mg | 60° |

Examples 13-15

Firstly, 0.65 g of N-methyl-3-aminopropyltrimethoxysilane was mixed with 1.83 g of α-acryloyl-ω-triethylsilylpropylpoly(ethylene glycol) [APC2] and left to stand for a period of 12 hours. According to $^1$H-NMR, corresponding to the radical content of double bonds of the acryloyl radical 85% of the Micheal addition product α-(N-methyl-N-(3-trimethoxysilylpropyl)-3-aminopropionyl)-ω-triethylsilylpropylpoly(ethylene glycol) had formed in the process. The product obtained in this way was mixed, in the amount given in Table 4, with 1.0 g of an α,ω-methyldimethoxysilyl-terminated polydimethylsiloxane with a viscosity of 80,000 mPas at 25° C. and 0.003 g of a tin catalyst (produced by reacting 4 parts by weight of tetraethoxysilane with 2.2 parts by weight of dibutyltin diacetate, with the ethyl acetate formed being distilled off) and poured into a small Petri dish such that for example a layer thickness of 1 mm was obtained. The material cures under the action of atmospheric humidity. After 24 hours, all of the mixtures had cured to a silicone elastomer. The contact angles of a water drop (20 μl) were then measured after 10 min. The results are summarized in Table 4.

TABLE 4

| Example | Amount of reaction product of [APC2] with N-methylaminopropyl-trimethoxysilane | Contact angle measured after 10 min |
|---|---|---|
| 13 | 82 mg | 45° |
| 14 | 41 mg | 54° |
| 15 | 21 mg | 60° |

Examples 16-18

10 g of an α,ω-methyldimethoxysilyl-terminated polydimethylsiloxane with a viscosity of 80,000 mPas were mixed, at 25° C., with the amounts, given in Table 5, of N-methyl-3-aminopropyltrimethoxysilane. Then, 0.03 g of a tin catalyst (produced by reacting 4 parts by weight of tetraethoxysilane with 2.2 parts by weight of dibutyltin diacetate, with the ethyl acetate formed being distilled off) was added and the mass was intensively mixed for 1 min and poured into a small Petri dish such that for example a layer thickness of 1 mm was obtained. The material cures under the action of atmospheric humidity. After 24 h, a 5% strength by mass solution of α-acryloyl-ω-triethylsilylpropylpoly(ethylene glycol) [APC2] in tetrahydrofuran was painted onto the surfaces of each sample. Firstly, a large excess of compound according to the invention was applied by applying the solution in abundance to the surface. The samples were stored for 10 h at room temperature, during which the tetrahydrofuran evaporated. The unreacted excess was then removed by placing the samples into methylene chloride 3 times for one hour in each case. The samples were then dried in each case in vacuo at 10 mbar. The contact angles of a water drop (20 μl) were then measured after 3 min. The results are summarized in Table 5.

TABLE 5

| Example | Amount of N-methylaminopropyl-trimethoxysilane | Contact angle measured after 3 min |
|---|---|---|
| 16 | 220 mg | 56 |
| 17 | 110 mg | 63 |
| 18 | 55 mg | 75 |

Examples 19-21

10 g of an α,ω-methyldimethoxysilyl-terminated polydimethylsiloxane with a viscosity of 80,000 mPas were mixed, at 25° C., with the amounts, given in Table 6, of 3-aminopropyltriethoxysilane. 0.03 g of a tin catalyst (produced by reacting 4 parts by weight of tetraethoxysilane with 2.2 parts by weight of dibutyltin diacetate, with the ethyl acetate formed being distilled off) was then added and the mass was intensively mixed for 1 min and poured into a small Petri dish such that for example a layer thickness of 1 mm was obtained. The material cures under the action of atmospheric humidity. After 24 h, a 5% strength by mass solution of α-acryloyl-ω-triethylsilylpropylpoly(ethylene glycol) [APC2] in tetrahydrofuran was painted onto the surfaces of each sample. Here, firstly a large excess of compound according to the invention was applied by applying the solution in abundance to the surface. The samples were stored for 10 h at room temperature, during which the tetrahydrofuran evaporated. The unreacted excess was then removed by placing the samples in methylene chloride 3 times for one hour in each case. The samples were then in each case dried in vacuo at 10 mbar. The contact angles of a water drop (20 μl) were then measured after 3 min. The results are summarized in Table 6.

TABLE 6

| Example | Amount of 3-aminopropyl-triethoxysilane | Contact angle measured after 10 min |
|---|---|---|
| 19 | 220 mg | 53 |
| 20 | 110 mg | 57 |
| 21 | 55 mg | 75 |

The invention claimed is:

1. A compound of the formula $$H_2C=C(R^2)-C(=O)-O-(CH_2CH_2O)_n-(CH_2CH_2CH_2)_m-Si(R^1)_3 \quad (I)$$

where
R$^1$ each individually is identical or different and is a hydrocarbon radical,
R$^2$ each individually is hydrogen or a methyl radical,
n is an integer from 6 to 11 and
m is 0 or 1,
with the proviso that the sum of the number of carbon atoms in the three radicals R$^1$ in the compound of the formula (I) is 6 to 24.

2. The compound of claim 1, wherein the radicals R$^1$ in formula (I) are the same.

3. The compound of claim 1, wherein the radicals R$^1$ are alkyl radicals having 1 to 12 carbon atoms.

4. A process for producing a compound of formula (I) of claim 1, comprising adding triorganylsilanes onto polyethylene glycols which carry an OH group on one end and have radicals with aliphatic carbon-carbon multiple bonds on the other end, in the presence of a catalyst promoting the addition of Si-bonded hydrogen onto an aliphatic multiple bond, and subsequently reacting with acryloyl chloride or methacryloyl chloride.

5. A process for producing a compound of formula (I) of claim 1, where m=0, comprising first reacting a hydroxymethyltriorganylsilane with ethylene oxide and a second step, reacting a resulting polyethylene glycol terminated at one end with a triorganylsilylmethyl group with acryloyl chloride or methacryloyl chloride.

6. A reaction product obtained by reacting a compound of claim 1 with an organosilicon compound (B) comprising at least one unit of the formula $$D_cSi(OR)_bR^3_aO_{(4-a-b-c)/2} \quad (II),$$

in which
R$^3$ each individually is identical or different and is a monovalent, optionally substituted, SiC-bonded organic radical free from basic nitrogen,
R each individually is identical or different and is hydrogen or an optionally substituted hydrocarbon radical,
D each individually is identical or different and is a monovalent, SiC-bonded radical comprising at least one group —NHR$^4$ where R$^4$ is hydrogen or an optionally substituted hydrocarbon radical,
a is 0, 1, 2 or 3,
b is 0, 1, 2 or 3 and
c is 0, 1, 2, 3 or 4,
with the proviso that the sum of a+b+c is less than or equal to 4 and organosilicon compound (B) comprises at least one radical of the formula (II) with at least one radical D.

7. A process for producing a reaction product of claim 6, comprising reacting a compound with an organosilicon compound (B) comprising at least one unit of the formula $$D_cSi(OR)_bR^3_aO_{(4-a-b-c)/2} \quad (II),$$

in which
R$^3$ each individually is identical or different and is a monovalent, optionally substituted, SiC-bonded organic radical free from basic nitrogen,
R each individually is identical or different and is hydrogen or an optionally substituted hydrocarbon radical,
D each individually is identical or different and is a monovalent, SiC-bonded radical comprising at least one group —NHR$^4$ where R$^4$ is hydrogen or an optionally substituted hydrocarbon radical,
a is 0, 1, 2 or 3,
b is 0, 1, 2 or 3 and
c is 0, 1, 2, 3 or 4,
with the proviso that the sum of a+b+c is less than or equal to 4 and organosilicon compound (B) comprises at least one radical of the formula (II) with at least one radical D.

8. The process of claim 7, wherein component (B) is a silane (B1) where a+b+c=4.

9. The process of claim 7, wherein component (B) is a siloxane (B2), containing at least one unit of the formula (II) where a+b+c≤3.

10. A process for modifying a surface of a substrate, comprising applying a reaction product produced by the process of claim 7 to the surface.

11. A crosslinkable composition comprising a reaction product of claim 6, or a compound of the formula (I) together with an organosilicon compound (B).

12. The crosslinkable composition of claim 11, which is a single-component composition storable with exclusion of water and crosslinkable at room temperature upon ingress of water (RTV-1).

13. A molding produced by crosslinking a composition of claim 11.

14. A process for modifying a surface of a substrate, comprising applying a reaction product of claim 6 to the surface of the substrate.

15. A process for modifying a surface of a substrate comprising applying a mixture of a compound of claim 1 and compound (B) to the surface, where compound (B) comprises at least one unit of the formula $$D_cSi(OR)_bR^3_aO_{(4-a-b-c)/2} \quad (II),$$

in which $R^3$ each individually is identical or different and is a monovalent, optionally substituted, SiC-bonded organic radical free from basic nitrogen, R each individually is identical or different and is hydrogen or an optionally substituted hydrocarbon radical, D each individually is identical or different and is a monovalent, SiC-bonded radical comprising at least one group —$NHR^4$ where $R^4$ is hydrogen or an optionally substituted hydrocarbon radical, a is 0, 1, 2 or 3, b is 0, 1, 2 or 3 and c is 0, 1, 2, 3 or 4, with the proviso that the sum of a+b+c is less than or equal to 4 and organosilicon compound (B) comprises at least one radical of the formula (II) with at least one radical D.

16. A process for modifying a surface of a substrate, comprising applying at least one compound of the formula (I)

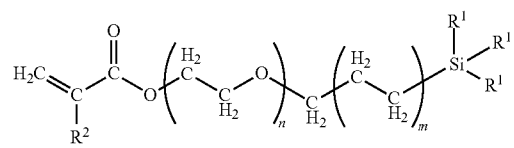

where $R^1$ each individually is identical or different and is a hydrocarbon radical, $R^2$ each individually is hydrogen or a methyl radical, n is an integer from 6 to 11 and m is 0 or 1, with the proviso that the sum of the number of carbon atoms in the three radicals $R^1$ in the compound of the formula (I) is 6 to 24, to the surface of a substrate which has groups which can react with an acrylic acid function.

* * * * *